United States Patent
Novo et al.

(10) Patent No.: US 9,981,951 B2
(45) Date of Patent: May 29, 2018

(54) CRYSTALLINE AND AMORPHOUS FORMS OF OLAPARIB

(71) Applicant: Olon S.P.A., Rodano (MI) (IT)

(72) Inventors: Barbara Novo, Rodano (IT); Jacopo Bonanomi, Rodano (IT); Stella Defiore, Rodano (IT); Francesco Calogero, Rodano (IT)

(73) Assignee: OLON S.P.A., Rodano (IT)

( * ) Notice: Subject to any disclaimer, the term of this patent is extended or adjusted under 35 U.S.C. 154(b) by 0 days. days.

(21) Appl. No.: 15/382,985

(22) Filed: Dec. 19, 2016

(65) Prior Publication Data

US 2017/0174662 A1     Jun. 22, 2017

(30) Foreign Application Priority Data

Dec. 22, 2015   (IT) .................. 102015000086616

(51) Int. Cl.
 *C07D 237/32*  (2006.01)
 *C07D 403/10*  (2006.01)

(52) U.S. Cl.
 CPC ......... *C07D 403/10* (2013.01); *C07D 237/32* (2013.01); *C07B 2200/13* (2013.01)

(58) Field of Classification Search
 CPC ........................... C07D 237/32; A61K 31/502
 USPC .................................. 544/236, 237; 514/248
 See application file for complete search history.

(56) References Cited

FOREIGN PATENT DOCUMENTS

WO   2008047082 A2   4/2008
WO   2009050469 A1   4/2009

OTHER PUBLICATIONS

Larsson A., et al., "Fragment-Based Ligand Design of Novel Potent Inhibitors of Tankyrases", Journal of Medicinal Chemistry, vol. 56, No. 11, Jun. 13, 2013, pp. 4497-4508.
Search Report and Written Opinion of IT UB20159206 dated May 11, 2016.

*Primary Examiner* — Venkataraman Balasubramanian
(74) *Attorney, Agent, or Firm* — Silvia Salvadori, P.C.; Silvia Salvadori (57) ABSTRACT

Disclosed are a novel crystalline form and an amorphous form of Olaparib, and the process for their preparation.

1 Claim, 7 Drawing Sheets

CRYSTALLINE AND AMORPHOUS FORMS OF OLAPARIB

This is a Non-Provisional Application claims priority to and the benefit of Italian Patent Application No. 102015000086616 filed on Dec. 22, 2015, the content of which is incorporated by reference in its entirety.

The present invention relates to a novel hydrated crystalline form (form B) and the amorphous form of Olaparib.

BACKGROUND OF THE INVENTION

PARP (poly ADP-ribose polymerase) inhibitors with a phthalazinone structure are known, in particular as BER (base excision repair) inhibitors. WO 2005/053662 discloses the use of said inhibitors for the treatment of tumor cells with an HR (homologous recombination) dependent DNA DSB (double-strand break) repair deficiency. In particular it describes the use of said compounds for tumors presenting a deficiency of phenotype BCRA1 and/or BCRA2, such as ovarian, breast or prostate cancer.

Olaparib (4-[3-(4-cyclopropanecarbonyl-piperazine-1-carbonyl)-4-fluorobenzyl]-2H-phthalazin-2-one), described in U.S. Pat. No. 7,449,464, is a PARP inhibitor used in the treatment of tumors, in combination with radiotherapy or chemotherapy.

Two crystalline forms of Olaparib, defined as form A and form L, are known in the literature. A solvated form of form A is also known.

Form A is described in U.S. Pat. No. 8,247,416. The crystalline form A of Olaparib has an XRPD spectrum ($\lambda$=1.5418 Å) containing the most intense peaks at 2$\theta$=10.5, 12.0, 14.0, 17.8, 21.1, 21.7, 22.3, 24.3, 26.1, 29.2.

The solvated crystalline form A, also described in U.S. Pat. No. 8,247,416, can be obtained by maturation and crystallization from different solvents. The XRPD spectrum ($\lambda$=1.5418 Å) of Olaparib as solvated form A has characteristic peaks at 2$\theta$=7.0-7.5, 10.1-10.6, 15.1-15.6, 18.5-19.0, 21.0-21.5, 24.8-25.3, 27.0-27.5.

Form L, disclosed in US 2010/286157, has an XRPD spectrum ($\lambda$=1.5418 Å) containing the most intense peaks at 2$\theta$=10.4, 13.6, 14.4, 17.2, 17.5, 18.8, 23.0, 25.1.

Particular crystalline forms of Olaparib can possess advantageous properties in terms of their solubility and/or stability and/or bioavailability and/or impurity profile and/or filtration characteristics and/or drying characteristics and/or their ability to be handled and/or micronized and/or preparation of solid oral forms.

DESCRIPTION OF THE INVENTION

The present invention relates to the preparation and characterization of a novel crystalline form (hydrated form B) and the amorphous form of Olaparib.

The amorphous form of Olaparib has better solubility in various organic solvents and in water than crystalline forms A and L of Olaparib. The amorphous form of Olaparib is stable if exposed to the moisture in the air, and is not hygroscopic.

The amorphous form of Olaparib is obtained from a suitable polar solvent such as methanol, dimethyl sulfoxide, dimethyl formamide, dimethyl acetamide, acetic acid and water, or from a suitable mixture thereof. Dimethyl sulfoxide, dimethylformamide or water is preferably used.

The amorphous form of Olaparib can be obtained by adding a solution of Olaparib in a polar solvent to an anti-solvent.

Olaparib in crystalline form is dissolved in a polar solvent such as methanol, dimethyl sulfoxide, dimethyl formamide, dimethylacetamide or acetic acid, preferably dimethyl sulfoxide, dimethylformamide or acetic acid, and more preferably dimethylsulfoxide or dimethylformamide, at a temperature ranging between 16° C. and 100° C., preferably between 20° C. and 70° C., and more preferably between 25° C. and 70° C.

The solution of Olaparib is added to an anti-solvent, preferably a polar protic anti-solvent such as water, at a temperature ranging between −10° C. and 50° C., preferably between −10° C. and 30° C., and more preferably between −10° C. and 25° C.

The resulting suspension is left under stirring for a time ranging between 0 and 5 hours, preferably between 10 minutes and 2 hours, and more preferably between 10 minutes and 40 minutes, at a temperature ranging between −20° C. and 50° C., preferably between −10° C. and 30° C., and more preferably between −10° C. and 25° C.

The suspension is filtered and the solid washed with an anti-solvent, preferably a polar protic anti-solvent such as water. The resulting solid is dried at low pressure at a temperature ranging between 0° C. and 70° C., preferably between 20° C. and 60° C.

Figure 1:
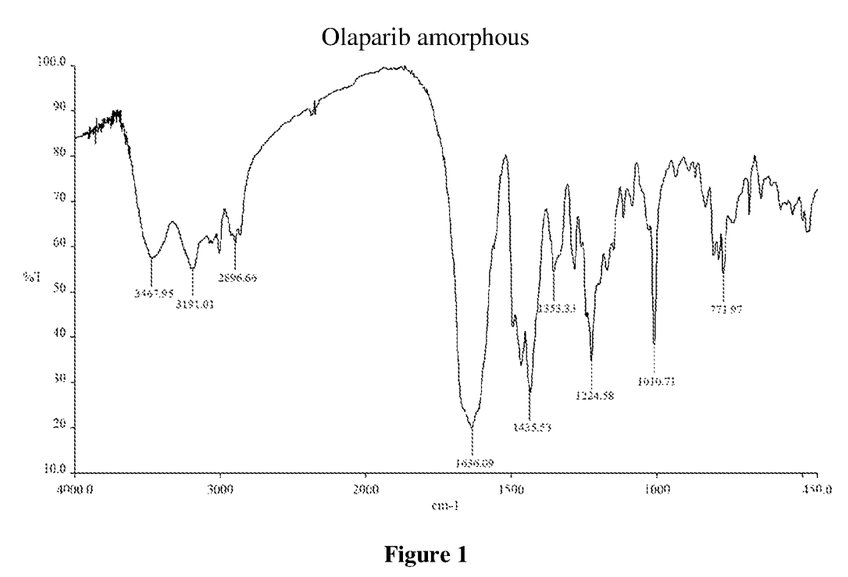
FIG. 1: Infrared spectrum of Olaparib amorphous form.
Figure 2:
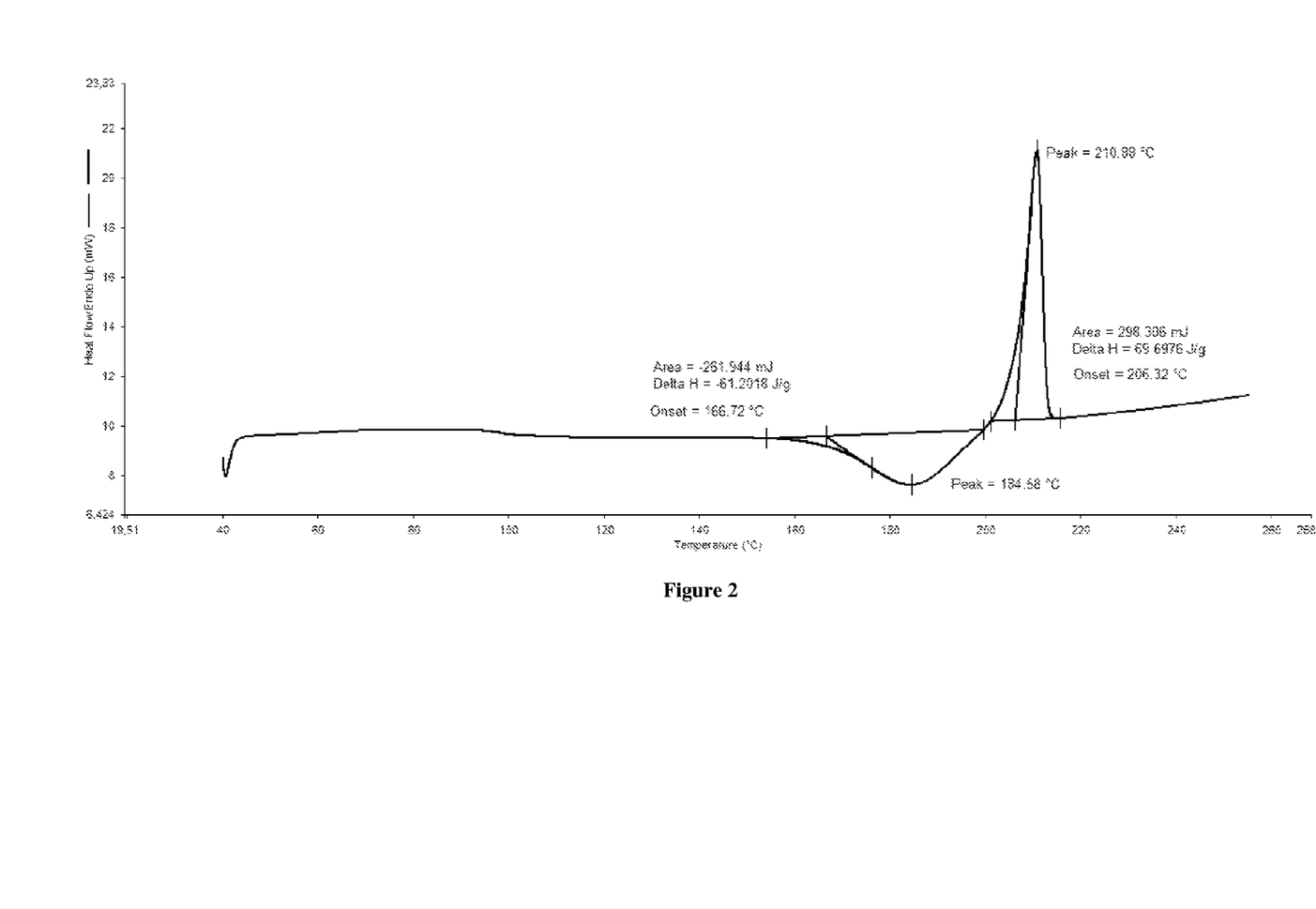
FIG. 2: DSC curve of Olaparib amorphous form.
Figure 3:
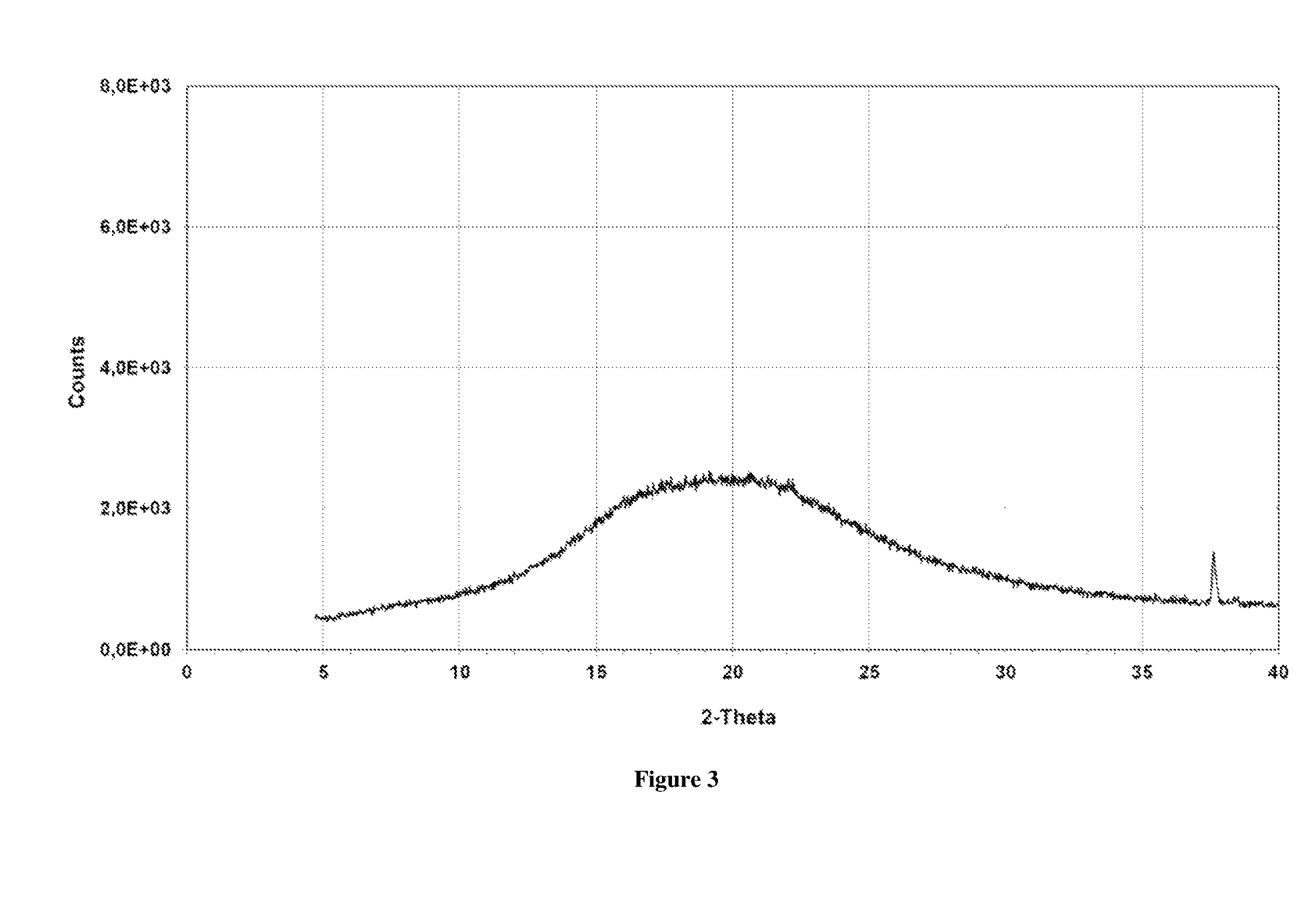
FIG. 3: XRPD pattern of Olaparib amorphous form.

The amorphous form of Olaparib has an IR spectrum, DSC curve and XRPD pattern as shown in FIGS. 1, 2 and 3 respectively.

In particular, the amorphous form of Olaparib has:
an IR spectrum comprising absorption peaks at ±1.5 cm$^{-1}$;
a DSC curve comprising an exothermic peak at 184.9° C. and an endothermic peak at 210.8° C.

Preparation of the Hydrated Crystalline Form of Olaparib (Form B):

The hydrated crystalline form of Olaparib (form B) exhibits better solubility in various organic solvents and in water than the crystalline forms of Olaparib A and L. The novel crystalline form is a hydrated form with a water content ranging between 3% and 7%. The water content aids the solubility of Olaparib in water. The hydrated crystalline form of Olaparib (form B) is stable to air and heat for a long time (30 days) and, when exposed to a water-saturated environment, maintains its original physicochemical characteristics.

The hydrated crystalline form of Olaparib (form B) is crystallized from a crystalline form of Olaparib (form A, form L or solvated form A) by a suitable polar solvent or a suitable mixture of polar solvents, such as carboxylic acids, amides and/or water.

The hydrated crystalline form of Olaparib (form B) can be obtained by adding a solution of Olaparib in a polar solvent to an anti-solvent, or adding an anti-solvent to a solution of Olaparib in a polar solvent.

The crystalline Olaparib is dissolved in a polar solvent such as acetic acid, propionic acid, butyric acid, valeric acid, dimethyl sulfoxide, dimethylformamide or dimethyl acetamide, preferably acetic acid, propionic acid, dimethylsulfoxide or dimethyl formamide, and more preferably acetic acid, dimethylsulfoxide or dimethylacetamide, at a temperature ranging between 20° C. and 100° C., preferably between 20° C. and 70° C., and more preferably between 35° C. and 70° C.

The solution of Olaparib is added to an anti-solvent, preferably a polar protic anti-solvent such as water, at a temperature ranging between −10° C. and 50° C., preferably between 0° C. and 30° C., and more preferably between 10° C. and 25° C.

Alternatively, an anti-solvent, preferably a polar protic anti-solvent such as water, is added to the Olaparib solution at a temperature ranging between −10° C. and 50° C., preferably between 0° C. and 30° C., and more preferably between 10° C. and 25° C.

The resulting suspension is left under stirring for a time ranging between 1 and 48 hours, preferably between 5 minutes and 24 hours, and more preferably between 10 minutes and 18 minutes, at a temperature ranging between 0° C. and 50° C., preferably between 10° C. and 40° C., and more preferably between 10° C. and 30° C.

The suspension is filtered and the solid washed with an anti-solvent, preferably a polar protic anti-solvent such as water. The resulting solid is dried at low pressure at a temperature ranging between 0° C. and 70° C., preferably between 20° C. and 60° C.

Alternatively, crystalline form B of Olaparib can be obtained from the amorphous form of Olaparib and a suitable mixture of polar solvents.

The amorphous form of Olaparib is treated with a polar solvent such as water, acetic acid, propionic acid, butyric acid, valeric acid, dimethylsulfoxide, dimethyl formamide or dimethyl acetamide, preferably acetic acid, propionic acid, dimethyl sulfoxide or dimethylformamide, and more preferably acetic acid, dimethylsulfoxide, dimethyl acetamide or a mixture thereof, at a temperature ranging between 20° C. and 100° C., preferably between 20° C. and 70° C., and more preferably between 35° C. and 70° C.

The resulting suspension is left under stirring for a time ranging between 1 and 48 hours, preferably between 5 minutes and 24 hours, and more preferably between 10 minutes and 18 minutes, at a temperature ranging between 0° C. and 50° C., preferably between 10° C. and 40° C., and more preferably between 10° C. and 30° C.

The suspension is filtered and the solid washed with an anti-solvent, preferably a polar protic anti-solvent such as water. The resulting solid is dried at low pressure at a temperature ranging between 0° C. and 70° C., preferably between 20° C. and 60° C.

Figure 4:
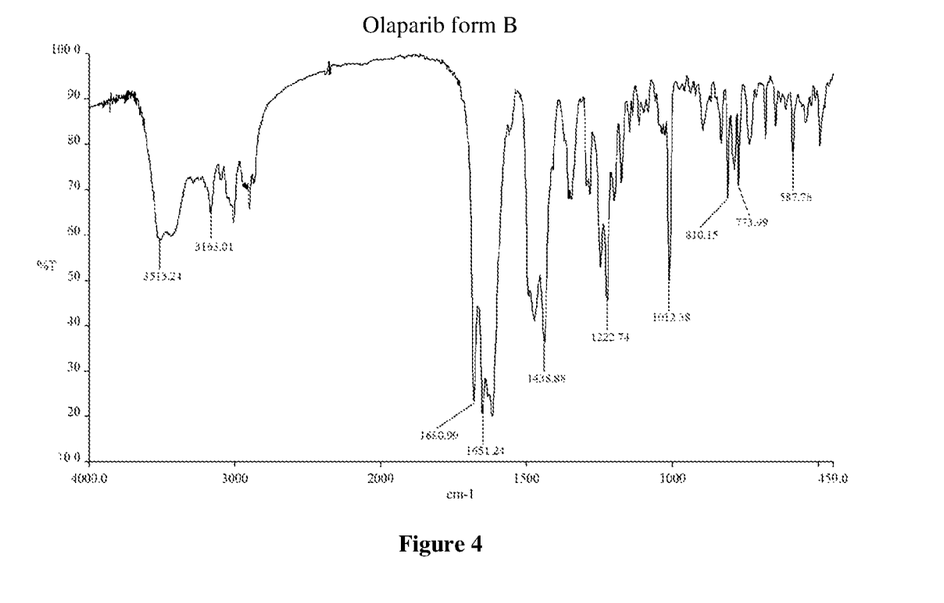
FIG. 4: Infrared spectrum of Olaparib crystalline form B.
Figure 5:
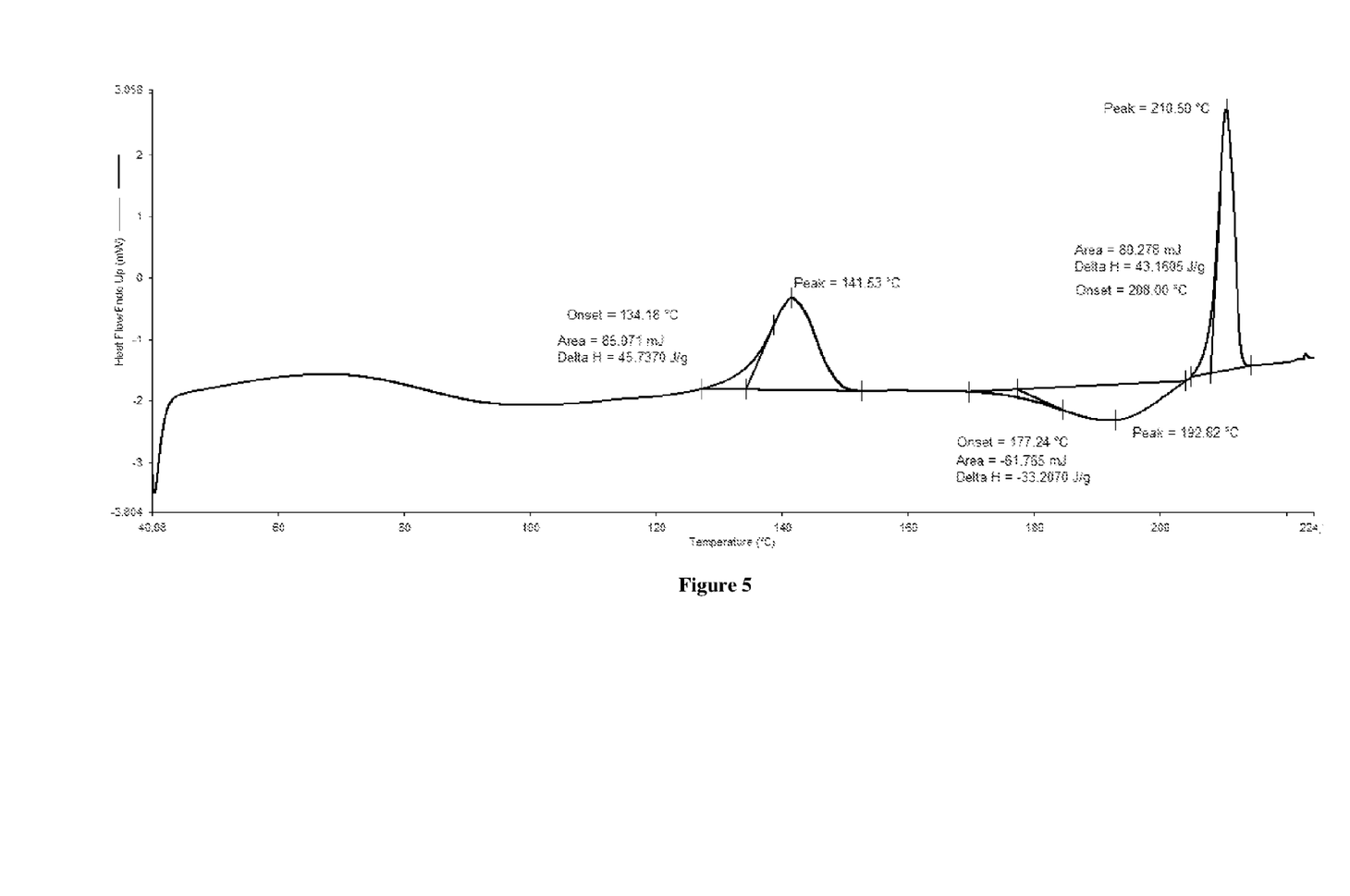
FIG. 5: DSC curve of Olaparib crystalline form B.
Figure 6:
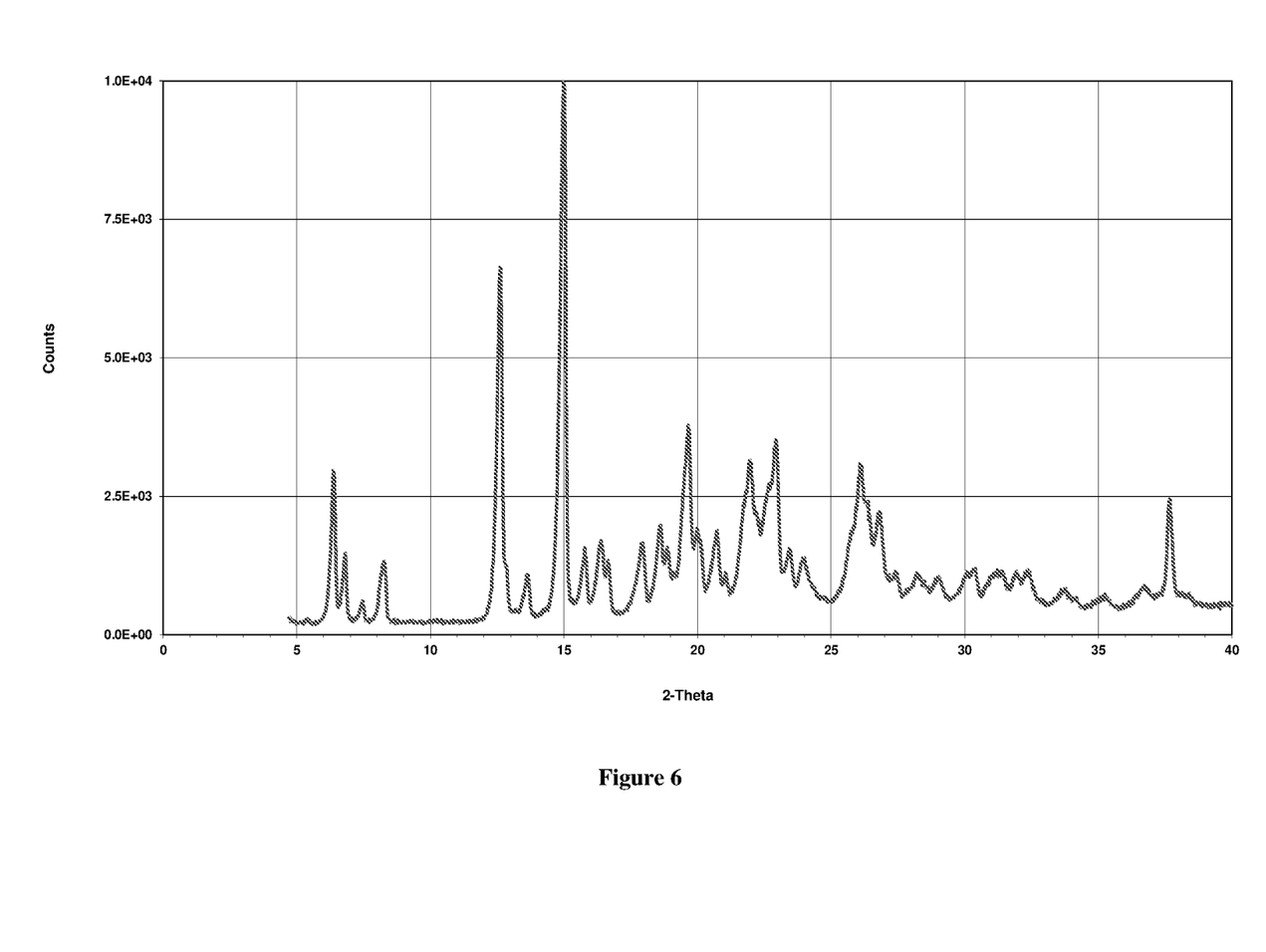
FIG. 6: XRPD pattern of Olaparib crystalline form B.
Figure 7:
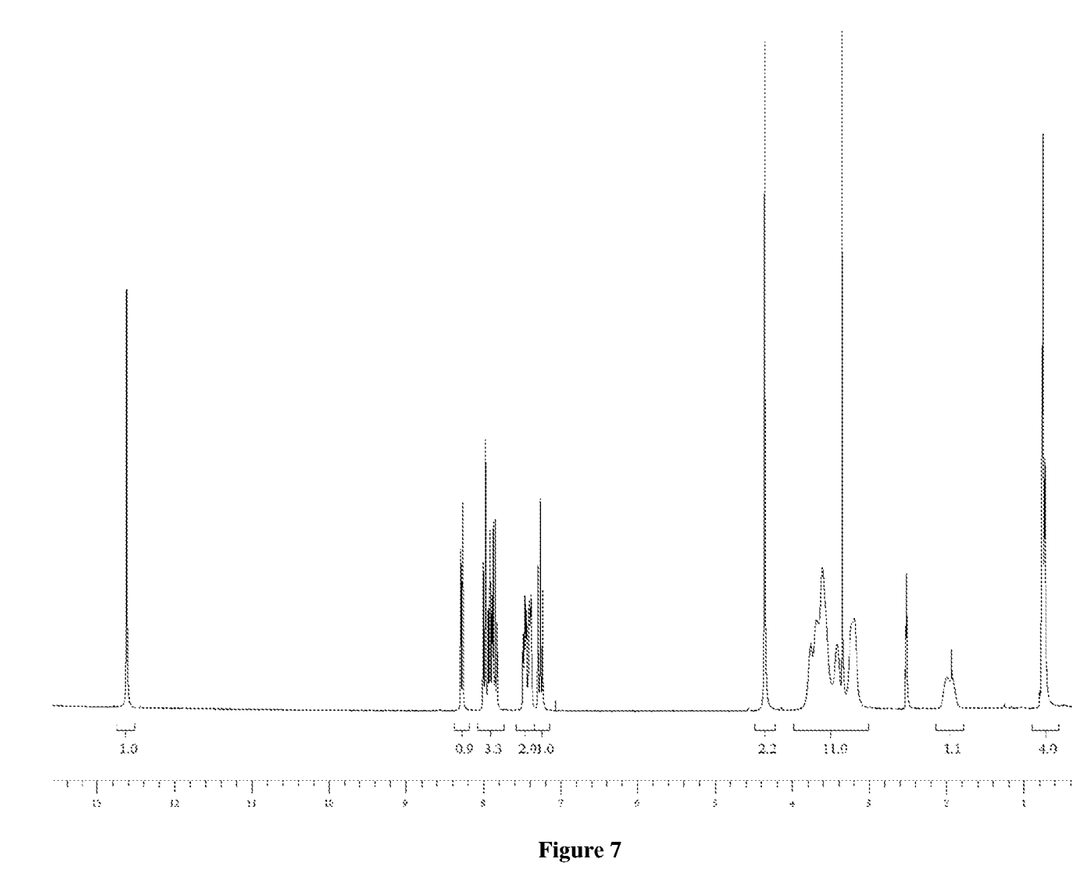
FIG. 7: $^1$H-NMR spectrum of the hydrated crystalline form of Olaparib (form B) in $d_6$-DMSO.

The hydrated crystalline form of Olaparib (form B) has an IR spectrum, DSC curve and XRPD pattern as shown in FIGS. 4, 5 and 6 respectively.

In particular, hydrated crystalline form B of Olaparib has:
an IR spectrum comprising absorption peaks at 3513, 3163, 1681, 1651, 1438, 1222, 1012, 810, 773, 587±1.5 cm$^{-1}$;
a DSC curve comprising an exothermic peak at 141.5° C. and an endothermic peak at 210.5° C.
An XRPD pattern comprising the following peaks: (2θ): 6.36 (29), 6.80 (14), 8.26 (13), 12.61 (65), 13.64 (10), 15.00 (100), 15.81 (14), 16.38 (17), 16.64 (13), 17.90 (16), 18.61 (20), 18.85 (15), 19.64 (37), 20.00 (19), 21.96 (31), 22.93 (35), 26.07 (30), 26.78 (22).

A Karl Fisher value ranging between 3% and 7%.

EXAMPLES

The IR spectra were recorded with a Perkin Elmer spectrum 1000 IR instrument, sample preparation as KBr pellet. The spectrum was recorded by performing 16 scans at a resolution of 4 cm$^{-1}$.

The DSC curves were recorded with a Perkin Elmer Pyris1 instrument; 3-5 mg of material was used to prepare the samples. The scans were conducted at the rate of 10° C. a minute.

The NMR spectra were recorded with a Varian Mercury 300 instrument in DMSO at 25° C., 16 scans being performed.

The XRPD spectra were recorded with a Bruker D2 instrument using the following parameters: Wavelength CuKα (λ=15419 Å)—Energy 30 KV—Stepsize: 0.02°—2θ Range: 2.6°-40°.

Example 1

Olaparib (1.0 g) is suspended in 3 ml of DMSO, and the suspension is heated at 60° C. until completely dissolved. The solution is poured into water (30.0 mL) at 0° C.

The resulting mixture is maintained under stirring for 30 minutes at 0° C., and filtered through a Büchner funnel to obtain 1.0 g of a white solid, which is dried in oven under vacuum for 10 h. The product (amorphous form) has an IR spectrum, DSC curve and XRPD pattern as shown in FIGS. 1-3 respectively.

Example 2

Olaparib (2.0 g) is suspended in 6 ml of DMF, and the suspension is heated at 60° C. until completely dissolved. The solution is poured into water (60.0 mL) at 0° C.

The resulting mixture is maintained under stirring for 30 minutes at 0° C., and filtered through a Büchner funnel to obtain 1.2 g of a white solid, which is dried in oven under vacuum for 1 h. The product (amorphous form) has an IR spectrum, DSC curve and XRPD pattern as shown in FIGS. 1-3 respectively.

Example 3

Olaparib (2.0 g) is suspended in 6 ml of acetic acid, and the suspension is heated at 50° C. until completely dissolved. The solution is poured into water (60.0 mL) at 0° C.

The resulting mixture is maintained under stirring for 16 h at 25° C., and filtered through a Büchner funnel to obtain 2.0 g of a white solid, which is dried in oven under vacuum for 24 h. The product (crystalline form B) has an IR spectrum, DSC curve, XRPD pattern and $^1$H-NMR spectrum as shown in FIGS. 4-7 respectively.

Example 4

Olaparib (2.0 g) is suspended in 6 ml of acetic acid, and the suspension is heated at 50° C. until completely dissolved. Water (60.0 mL) is added by dripping at 0° C. The resulting mixture is maintained under stirring for 16 h at 25° C., and filtered through a Büchner funnel to obtain 2.0 g of a white solid, which is dried in oven under vacuum for 24 h. The product (crystalline form B) has an IR spectrum, DSC curve, XRPD pattern and $^1$H-NMR spectrum as shown in FIGS. 4-7 respectively.

Example 5

The amorphous form of Olaparib obtained in example 1 (1.0 g) is suspended in 10 ml of a 3/7 mixture of acetic acid/water. The suspension is maintained under stirring for 16 h at 25° C., and filtered through a Büchner funnel to obtain 0.9 g of a white solid, which is dried in oven under vacuum for 24 h. The product (crystalline form B) has an IR spectrum, DSC curve, XRPD pattern and $^1$H-NMR spectrum as shown in FIGS. 4-7 respectively.

Example 6

Olaparib form A (2.0 g) is suspended in 60 ml of water and seeded with Olaparib form B. The suspension is maintained under stirring at 25° C. for 7 days. The suspension is filtered through a Bëchner funnel to obtain 2.0 g of a white solid, which is dried in oven under vacuum for 24 h. The product (crystalline form B) has an IR spectrum, DSC curve, XRPD pattern and $^1$H-NMR spectrum as shown in FIGS. 4-7 respectively.

The invention claimed is:

1. Hydrated crystalline form B of Olaparib, wherein:
   IR spectrum comprises absorption peaks at 3513, 3163, 1681, 1651, 1438, 1222, 1012, 810, 773, 587±1.5 cm-1;
   DSC curve comprises an exothermic peak at 141.5° C. and an endothermic peak at 210.5° C.;
   XRPD pattern comprises the following peaks: (2θ): 6.36 (29), 6.80 (14), 8.26 (13), 12.61 (65), 13.64 (10), 15.00 (100), 15.81 (14), 16.38 (17), 16.64 (13), 17.90 (16), 18.61 (20), 18.85 (15), 19.64 (37), 20.00 (19), 21.96 (31), 22.93 (35), 26.07 (30), 26.78 (22);
   Karl Fisher value ranges from 3% to 7%.

* * * * *